(12) United States Patent
Mattson (10) Patent No.: US 10,583,030 B2
(45) Date of Patent: Mar. 10, 2020

(54) SLEEP DEVICE

(71) Applicant: Larry J. Mattson, Lake Wylie, SC (US)

(72) Inventor: Larry J. Mattson, Lake Wylie, SC (US)

( * ) Notice: Subject to any disclaimer, the term of this patent is extended or adjusted under 35 U.S.C. 154(b) by 304 days.

(21) Appl. No.: 15/161,343

(22) Filed: May 23, 2016

(65) Prior Publication Data
US 2016/0346113 A1 Dec. 1, 2016

Related U.S. Application Data

(60) Provisional application No. 62/167,586, filed on May 28, 2015.

(51) Int. Cl.
*A61F 5/56* (2006.01)
*A47G 9/10* (2006.01)

(52) U.S. Cl.
CPC .............. *A61F 5/56* (2013.01); *A47G 9/10* (2013.01); *A47G 2009/1018* (2013.01)

(58) Field of Classification Search
CPC .... A47G 2009/1018; A47G 9/00; A47G 9/10; A47G 9/1045; A47G 9/1054; A61F 5/56; A47C 7/383
See application file for complete search history.

(56) References Cited

U.S. PATENT DOCUMENTS

| | | | |
|---|---|---|---|
| 1,580,210 A * | 4/1926 | McCulloch | A47G 9/10 5/636 |
| 3,141,179 A * | 7/1964 | McLean | A47C 21/003 5/636 |
| 3,312,987 A | 4/1967 | Emery | |
| 3,574,397 A | 4/1971 | Norriss | |
| 3,667,074 A | 6/1972 | Emery | |
| 4,349,925 A | 9/1982 | Macomber | |
| 4,788,728 A | 12/1988 | Lake | |
| 5,457,832 A | 10/1995 | Tatum | |
| 5,481,771 A | 1/1996 | Burk, IV | |
| 5,528,784 A | 6/1996 | Painter | |
| 5,615,432 A | 4/1997 | Von Ohlen, III | |
| 5,636,638 A | 6/1997 | Carlson et al. | |
| 5,642,543 A * | 7/1997 | Huntley | A47G 9/10 5/490 |
| 5,781,947 A * | 7/1998 | Sramek | A47G 9/10 5/636 |
| 6,230,349 B1 | 5/2001 | Silver et al. | |
| 6,622,325 B1 | 9/2003 | Garza | |
| 6,913,019 B2 | 7/2005 | Johns et al. | |
| 7,469,435 B1 | 12/2008 | Cullifer | |
| D597,364 S | 8/2009 | Lindgren | |

(Continued)

Primary Examiner — Nicholas F Polito (57) ABSTRACT

The present invention provides methods and systems for a sleep device that includes a core having a top portion, a bottom portion, a top side, a bottom side, a first side, and a second side. A first padded surface covers the top portion of the core, and a second padded surface covers the bottom portion of the core. The top side is generally linear and extends to a first end and a second end on either side of the top side, a first side extends downwardly from the first end and a second side extends downwardly from a second end, the first end and second end extends downwardly to a bottom side, wherein the bottom side contains two-spaced apart knobs and centrally located cavity between the two spaced-apart knobs.

6 Claims, 6 Drawing Sheets

(56) References Cited

U.S. PATENT DOCUMENTS

| | | | |
|---|---|---|---|
| 7,594,288 B1 * | 9/2009 | Holliday | A47G 9/10 5/630 |
| 7,594,289 B1 | 9/2009 | Medlock | |
| 7,707,668 B2 | 5/2010 | Kloes et al. | |
| 8,516,639 B2 | 8/2013 | Mobley et al. | |
| 8,813,283 B2 | 8/2014 | Alexander | |
| 8,856,991 B2 | 10/2014 | Edwards et al. | |
| 9,009,897 B2 | 4/2015 | Davis et al. | |
| 2002/0050007 A1 | 5/2002 | Kim | |
| 2005/0076442 A1 * | 4/2005 | Wassilefky | A47G 9/10 5/636 |
| 2005/0102759 A1 | 5/2005 | Myrick | |
| 2006/0016011 A1 | 1/2006 | Berg | |
| 2006/0037142 A1 * | 2/2006 | Binder | A47G 9/10 5/644 |
| 2007/0056108 A1 * | 3/2007 | Nikolopoulos | A61H 37/00 5/644 |
| 2007/0283495 A1 | 12/2007 | Ghani | |
| 2008/0155752 A1 * | 7/2008 | Fujita | A47G 9/109 5/636 |
| 2008/0216242 A1 | 9/2008 | Reeves | |
| 2012/0073056 A1 * | 3/2012 | Freund | A47G 9/0253 5/639 |
| 2013/0098364 A1 * | 4/2013 | Davis | A47G 9/1081 128/206.21 |
| 2013/0145556 A1 * | 6/2013 | Kummerfeld | A47D 13/00 5/655 |
| 2013/0232693 A1 | 9/2013 | Myers | |
| 2013/0254999 A1 * | 10/2013 | Foch | A47G 9/10 5/639 |
| 2013/0291306 A1 * | 11/2013 | Willingham | A47G 9/10 5/636 |
| 2013/0291308 A1 * | 11/2013 | Kiefer | A47C 20/00 5/652.1 |
| 2013/0305456 A1 | 11/2013 | Thompson | |
| 2014/0310877 A1 * | 10/2014 | Sternlight | A47G 9/10 5/639 |
| 2014/0359947 A1 | 12/2014 | Turner | |
| 2015/0101125 A1 * | 4/2015 | Fang | A47D 13/083 5/655 |
| 2016/0022063 A1 * | 1/2016 | Fulkerson | A47G 9/10 5/636 |
| 2016/0263386 A1 * | 9/2016 | Vansickle | A61N 1/0551 |

\* cited by examiner

SLEEP DEVICE

CROSS REFERENCE TO RELATED PATENT APPLICATION

The present patent application/patent claims the benefit of priority of U.S. Provisional Patent Application No. 62/167,586, filed on May 28, 2015, and entitled "SLEEP DISK," the contents of which are incorporated in full by reference herein.

FIELD OF THE INVENTION

The present invention relates generally to a device for keeping bedding material away from the face of an individual sleeping, while allowing the individual to breathe unobstructed and for freer breathing, and more generally relates to a sleep device for engaging the side of a user's head, allowing the bone structure to provide support for a shield to protect the face without putting undo pressure on the ear, and to keep bedding away from the face of the user.

BACKGROUND OF THE INVENTION

Obstruction of the breathing passages occurs when a person is sleeping on their side, the most common position, and a pillow or other bedding distorts the normal shape and structure of the face. This causes a collapse of the airways on the side of the face against the pillow and greatly reduces the body ability to take in oxygen.

Optimizing the intake of oxygen while a person is asleep is essential to good health. Oxygen facilitates the healthy regeneration of all of the body's mussels and organs including and most importantly the brain.

Snoring can also occur when air cannot freely move through the nose during sleep. Snoring is an indicator of obstructed breathing and is often caused by the narrowing of the airway, either from poor sleep posture or the distortion of the soft tissue in the face or throat. The poor posture or distortion of the soft tissue of the face restricts or narrows the airway and creates the need to breathe thru the mouth, drying out the tissue in the throat causing snoring.

Therefore, there is a need for a device that is easy to use and effective in allowing for freer breathing. The present invention solves this need with a lightweight, easy to use, and effective device to prevent obstruction of the breathing passages in the soft tissue of the face.

BRIEF SUMMARY OF THE INVENTION

According to an embodiment of the present invention, a sleep device includes a core having a top portion, a bottom portion, a top side, a bottom side, a first side, and a second side. A first padded surface covers the top portion of the core, and a second padded surface covers the bottom portion of the core. The top side is generally linear and extends to a first end and a second end on either side of the top side, a first side extends downwardly from the first end and a second side extends downwardly from a second end, the first side and second side extends downwardly to a bottom side, wherein the bottom side contains two-spaced apart knobs and centrally located cavity between the two spaced-apart knobs.

According to an embodiment of the present invention, a sleep device includes a top portion and a bottom portion for placement adjacent the face of a user for preventing bedding from contacting the user's face during sleeping.

According to an embodiment of the present invention, a sleep device includes a top portion, a bottom portion, a top side, a bottom side, a first side, and a second side.

According to an embodiment of the present invention, a sleep device includes a top side that extends to a first side and a second side, the first side extends downwardly to a bottom side and the second side extends downwardly to the bottom side.

According to an embodiment of the present invention, a sleep device includes a bottom side that includes two spaced-apart knobs and a cavity disposed between the two spaced-apart knobs.

According to an embodiment of the present invention, a sleep device includes a first foam layer engaged to a top portion of the sleep device and a second foam layer engaged to the bottom portion of the sleep device.

According to another embodiment of the present invention, the sleep device includes a core composed of HDPE.

According to yet another embodiment of the present invention, the sleep device includes a first foamed layer composed of HDPE and a second foamed layer composed of foamed HDPE or other acceptable padding, such as polyurethane foam.

According to yet another embodiment of the present invention, the sleep device includes polyester batting material.

According to yet another embodiment of the present invention, the sleep device includes two spaced-apart knobs that are arcuate shaped.

According to yet another embodiment of the present invention, the sleep device includes a length between about 2 inches to about 10 inches.

According to yet another embodiment of the present invention, the sleep device includes a first padded surface and a second padded surface that is about ¼ inch thick.

According to yet another embodiment of the present invention, a method of preventing bedding from contacting the face of a user that includes providing a sleep device with a core having a top portion, a bottom portion, a top side, a bottom side, a first side, and a second side. The sleep device is placed on bedding or pillow of a bed, and a user's cheek is placed on the top portion of the sleep device.

According to yet another embodiment of the present invention, the sleep device includes placing the user's ear within the cavity.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
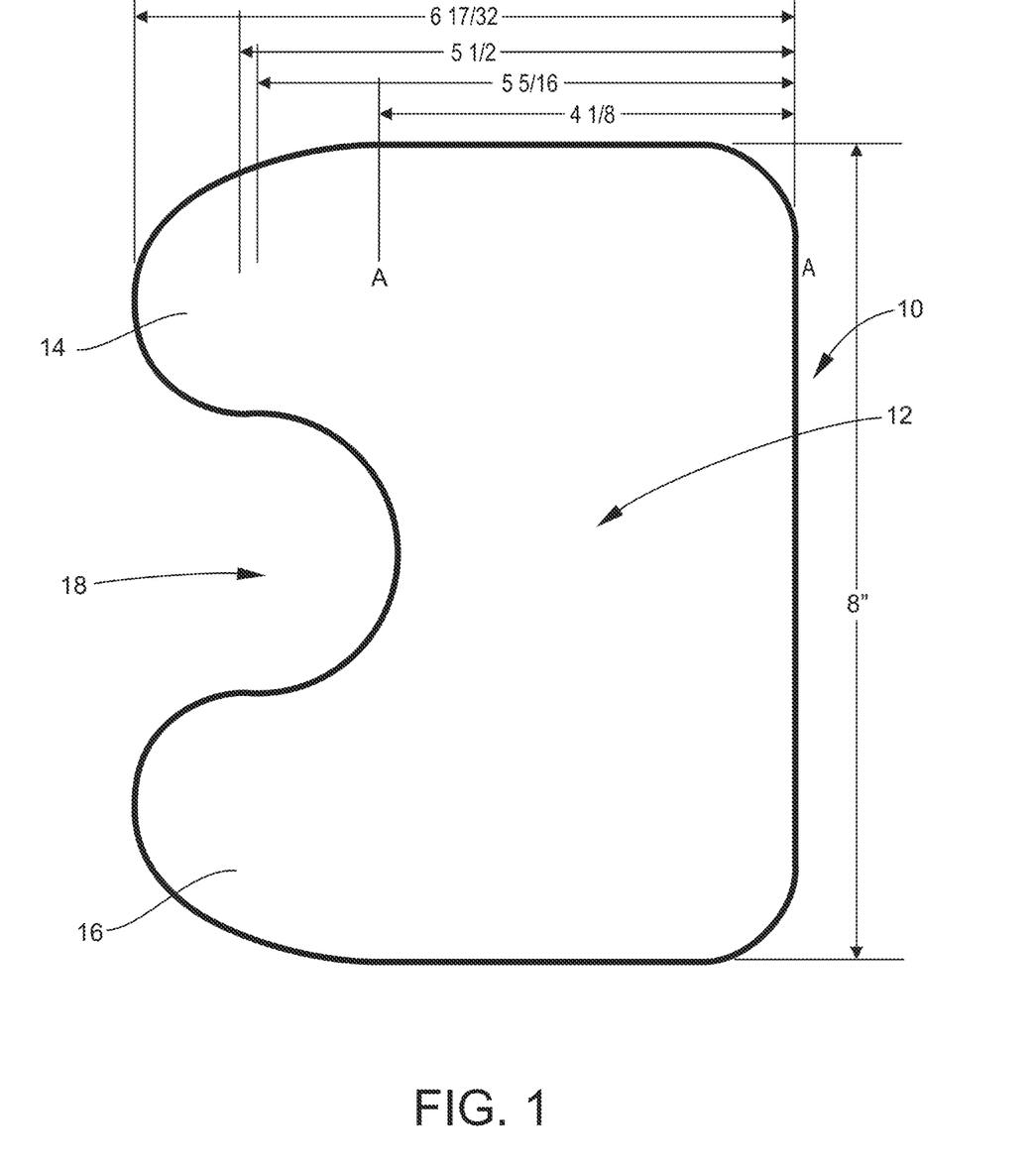
FIG. 1 is a top view of the sleep device.

Referring now specifically to the figures, a sleep device 10 that aids in preventing bedding material, such as sheets, pillows, and blankets, away from a user's face during sleeping is illustrated in FIG. 1 and is shown generally at reference numeral 10. The sleep device 10 engages the side of a user's head, allowing the bone structure to provide support for a shield to protect the face without putting undo pressure on the ear, and at the same time preventing bedding material from obstructing a user's face during sleeping. The sleep device 10 provides for easier breathing during deep sleep cycles.

Figure 3:
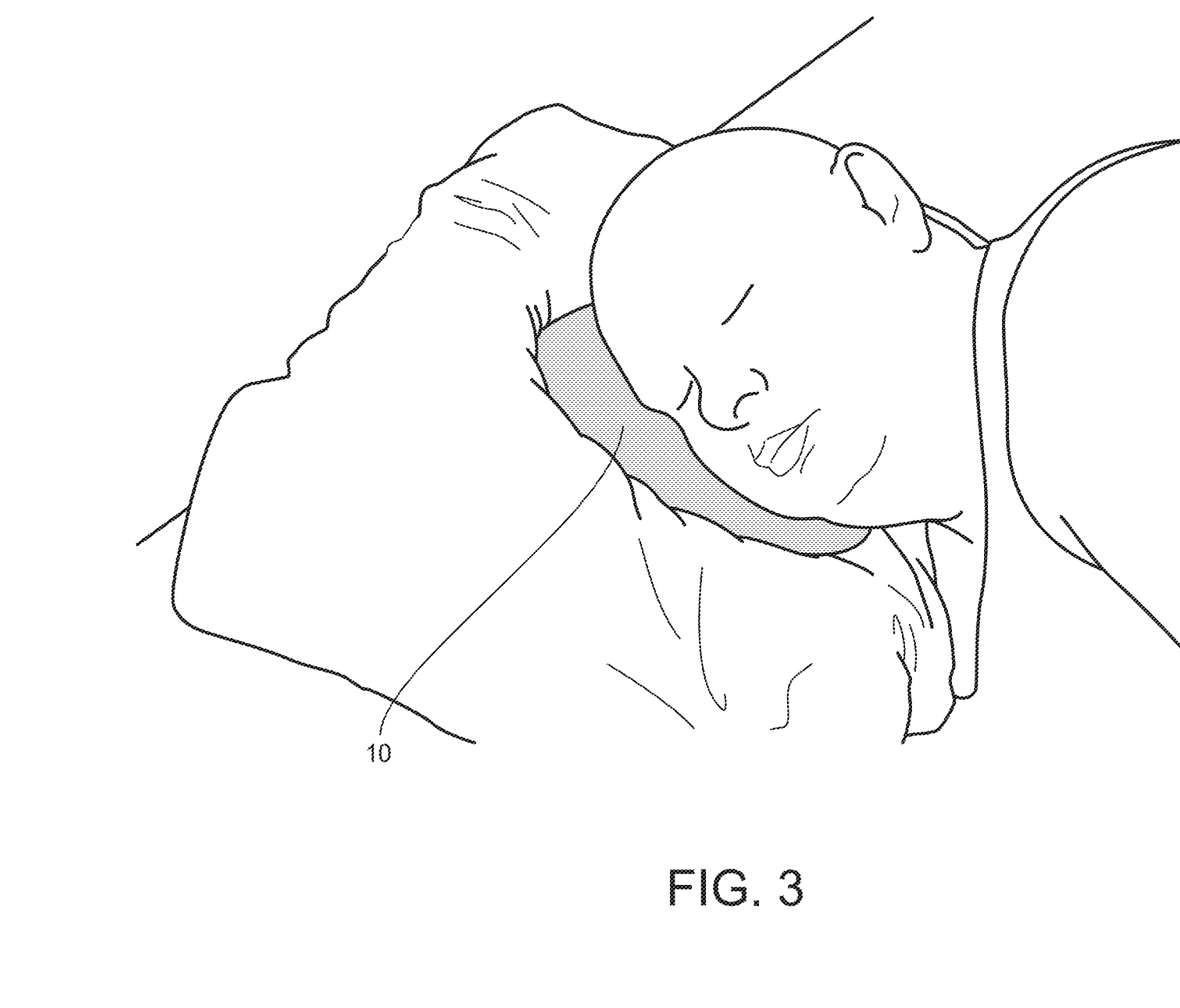
FIG. 3 is an example of the sleep device in use.

An exemplary embodiment of a sleep device 10 is illustrated in FIG. 1. The sleep device 10 basically comprises a central portion 12 for contacting the cheek of the user. As best seen in FIG. 3, the central portion 12 is, in operation of use of the present invention, placed against a portion of the individual and, in its preferred use against the cheek of the individual. Attached to and extending from the central portion 12 are two outwardly extending knobs 14 and 16. In the preferred embodiment of the present invention, these knobs 14, 16 are substantially uninterrupted extensions of the central portion 12. The knobs 14, 16 are separated by a generally concentrically shaped cavity 18 for placing and receiving the ear of a user. The cavity 18 is an open space between the two knobs 14, 16 for the user to place his/her ear while his/her cheek is resting on the central portion 12 of the device 10.

In one embodiment, the sleep device 10 generally has a top portion, a bottom portion, a top side, a bottom side, a first side, and a second side. The top side is generally flat and extends in one direction to a corner between the top side and the first side and in the other direction to a corner between the top side and the second side. The corners between the top side and first side and top side and second side are generally rounded without a point. The first side and second side extends generally downward from the corner of the top side to the knobs 14, 16. The bottom side consists of the knobs 14, 16 and cavity 18.

The preferred dimensions of the sleep device 10 are illustrated in FIG. 1. However, it should be noted other dimensions may be utilized. For example, the length of the sleep device may be between about 2 inches to about 10 inches, preferably between about 4 inches to about 9 inches, and more preferably about 8 inches. The distance between A-A, as illustrated in FIG. 1, may be between about 1 inch to about 6 inches, preferably between about 2 inches to about 5 inches, and more preferably about 4⅛ inches. The radius of curvature of the corners is between about 0.5 inches to about 2 inches, and preferably about 1 inch.

The radius of curvature of the cavity 18 is between about 0.1 inch and 3 inches, preferably between about 0.2 inches and 2 inches, and more preferably 1¹³⁄₃₂". The radius of curvature of the knobs 14, 16 have various radii of curvature throughout its length. The first part of the knob 14, 16 that transitions from the first side or second side to the knob has a radius of curvature of between about 1 inch and 6 inches, preferably between about 2 inches and 5 inches, and more preferably 4 inches. The radius of curvature at the outermost portion of the knob 14, 16 is between about 0.5 inch to about 4.5 inches, preferably about 1 inch to about 2.5 inches, and more preferably 1¹³⁄₃₂ inches. The radius of curvature for the portion of the knob 14, 16 between the outermost portion of the knob 14, 16 to the cavity 18 is between about 0.1 inches to about 4 inches, more preferably between about 0.5 inches to about 3 inches, and more preferably about 1 inch. The width of the device 10 is preferably between about 4 inches and about 8 inches, more preferably between about 5 inches and about 7 inches, most preferably about 6¹⁷⁄₃₂ inches.

Figure 2:
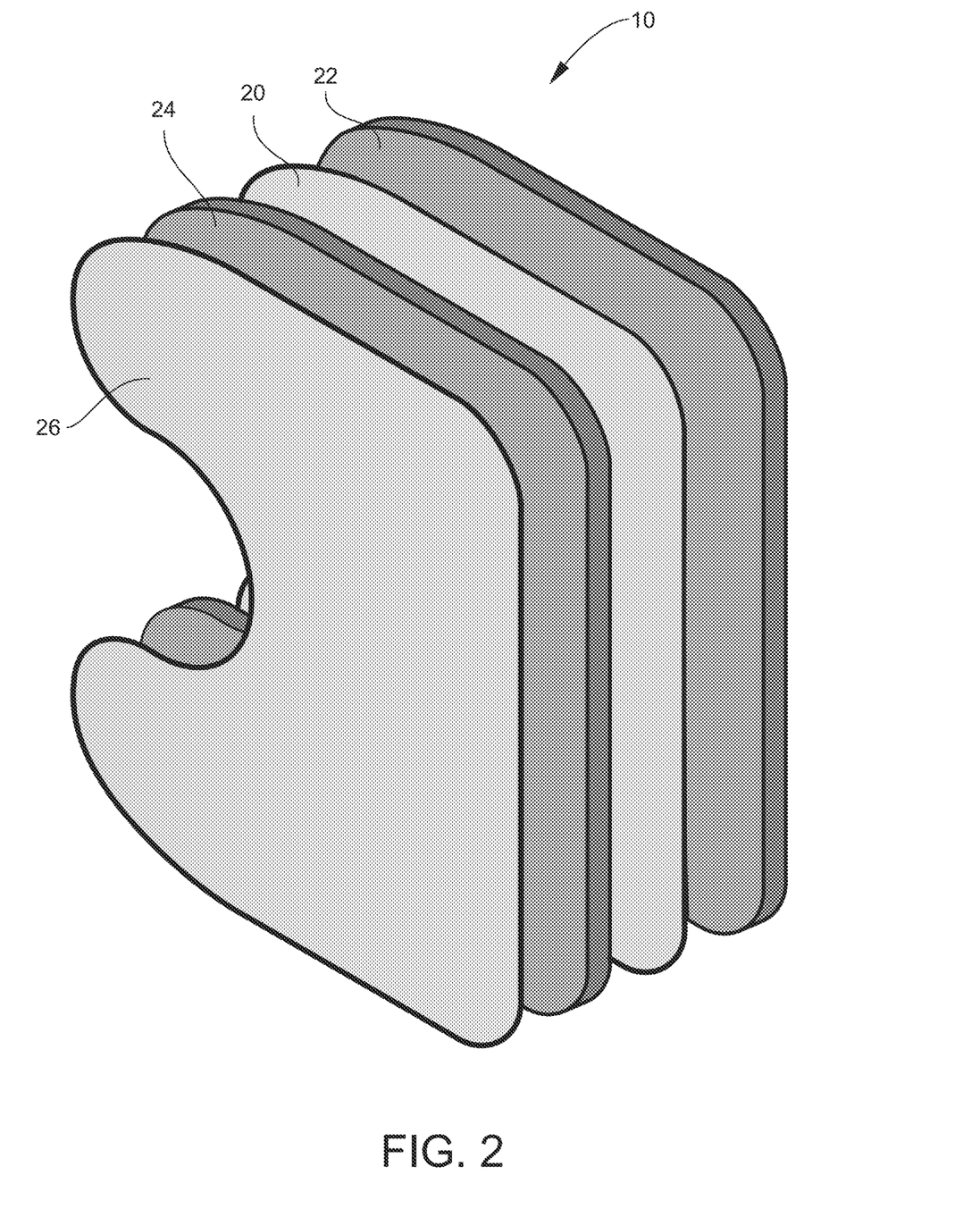
FIG. 2 is an exploded view of the sleep device.

As illustrated in FIG. 2, the sleep device 10 has a core 20, preferably composed of HDPE (high density polyethylene), and the core 20 is enclosed in a first layer of foam 22 (or first padded layer), such as an HDPE padded foam, and a second layer of foam 24 (or second padded layer), such as a polyurethane foam. The second layer of foam 24 is engaged to a polyester batting material 26. In this arrangement, the top portion is the polyester batting material 26 and the bottom portion is the first layer of foam 22. In one embodiment, the first layer of foam 22 is preferably between about 0.1 inch to about 1 inch thick, and more preferably about ¼ inch thick. The core 20 is preferably between about 0.01 inch to about 1 inch thick, and more preferably about ¹⁄₁₆ inch thick. The second layer of foam 24 is preferably between about 0.1 inch to about 1 inch thick, and more preferably about ¼ inch thick. The polyester batting material 26 is preferably between about 0.01 inch to about 1 inch thick, and more preferably about ¹⁄₁₆ inch thick. The core 20, first layer of foam 22, second layer of foam 24, and polyester batting material 26 are retained together by an adhesive, fastener, or the like. Any other suitable material that is semi-rigid may be utilized as the core, instead of an HDPE core. Additionally, any suitable material that is padded or foamed may be utilized as the first padded layer or second padded layer to provide a cushion for the user. In another alternative embodiment, the sleep device 10 just contains a core without any padding covering the core. The first layer of foam 22, second layer of foam 24, and polyester batting material 26 may have the same shape as the core 20.

The core 20 may contain a plurality or ribs or spacers engaging the top side to the bottom side. In this embodiment, air is able to pass through spaces within the ribs or spacers.

In use, the sleep device 10 is laid upon a pillow or mattress. The sleep device 10 prevents the pillow or bedding from exerting pressure on the side of the face, resulting in the collapse of breathing passages and unsetting the jaw, while at the same time allowing the ear to rest comfortably against the bedding. The device 10 restricts the pillow or bedding from contacting the user's face, nose, or mouth. The device 10 discourages mouth breathing, resulting in less snoring, by keeping the nasal passages open and allowing the jaw to remain comfortably closed. Even though the sleep device 10 discourages mouth breathing, it allows the body to receive a sufficient flow of oxygen.

In another alternative embodiment, the device 10 may be a single injection molded part instead of having multiple pieces. The device 10, by way of the core 20 may have different levels of rigidity. The levels of rigidity will be based upon a user's preference and color coded accordingly. The rigidity may span from being semi-rigid to rigid. By way of example only, the color red could be used to indicate the most rigid device 10, and progress through green, yellow, blue, and orange, whereby orange would indicate the less rigid device 10.

The key features of the sleep device 10 are:
i. light
ii. thin
iii. one size fits all
iv. works with any shape, size, or filled pillow
v. simple to use
vi. easy to sanitize
vii. hypoallergenic
viii. easy to pack and take with you
ix. keeps face away from pillow others have slept on previously
x. economical The key benefits of the sleep device 10 are:
i. unobstructed breathing while sleeping
ii. better sleep
iii. less snoring
iv. higher oxygen levels while asleep
v. use the sleep device anywhere
vi. works on either the left or right side of the user
vii. allows the user to breath clean air The device 10 may be enclosed in an outer case or covering. The covering has an end that allows the device 10 to be easily inserted into the case and removed from the case. The case includes a cavity for retaining the device and an open end that is closeable through a fastening device, such as a zipper, buttons, and the like. Additionally, a pocket may be positioned on a pillowcase, for allowing the device 10 to be inserted and retained within the pillowcase for use by a user.

Figure 4:
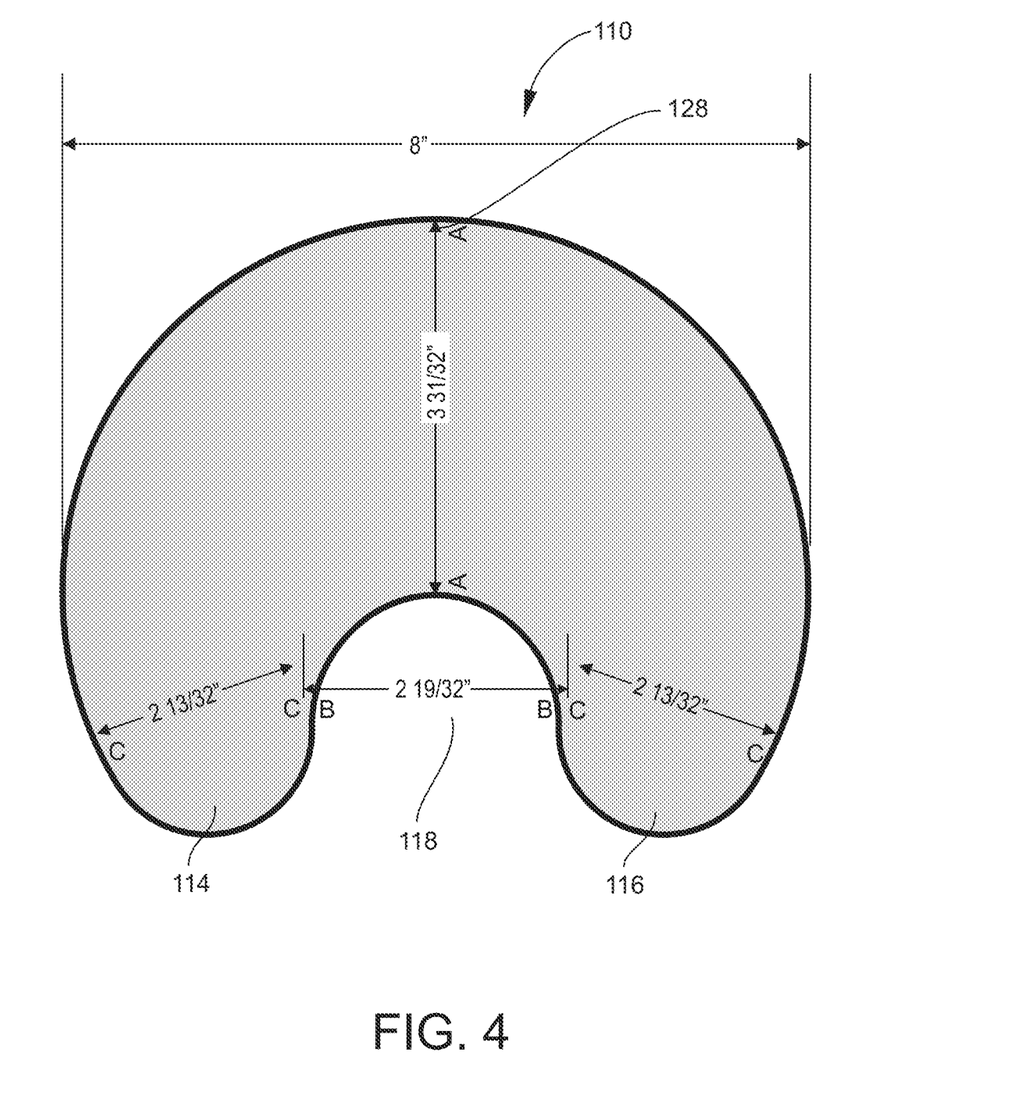
FIG. 4 is a top view of an alternative embodiment of the sleep device.
Figure 5:
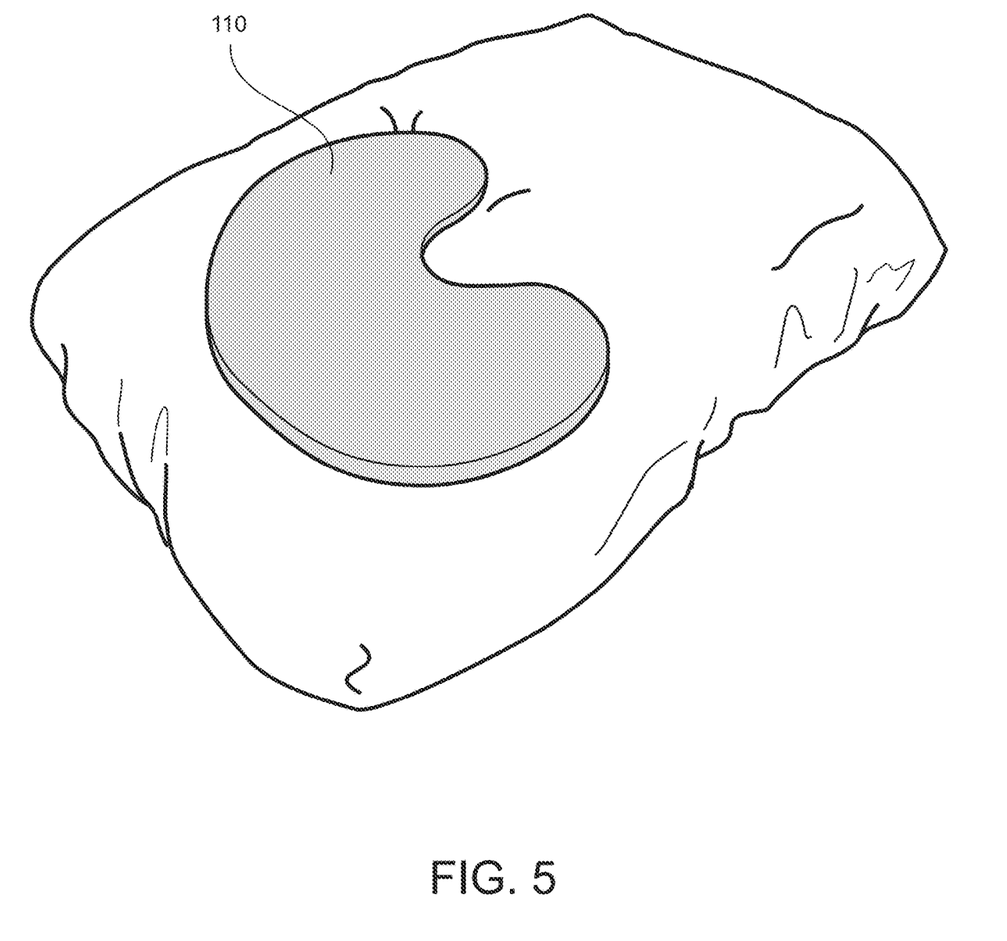
FIG. 5 is a perspective view of an alternative embodiment of the sleep device on a pillow.
Figure 6:
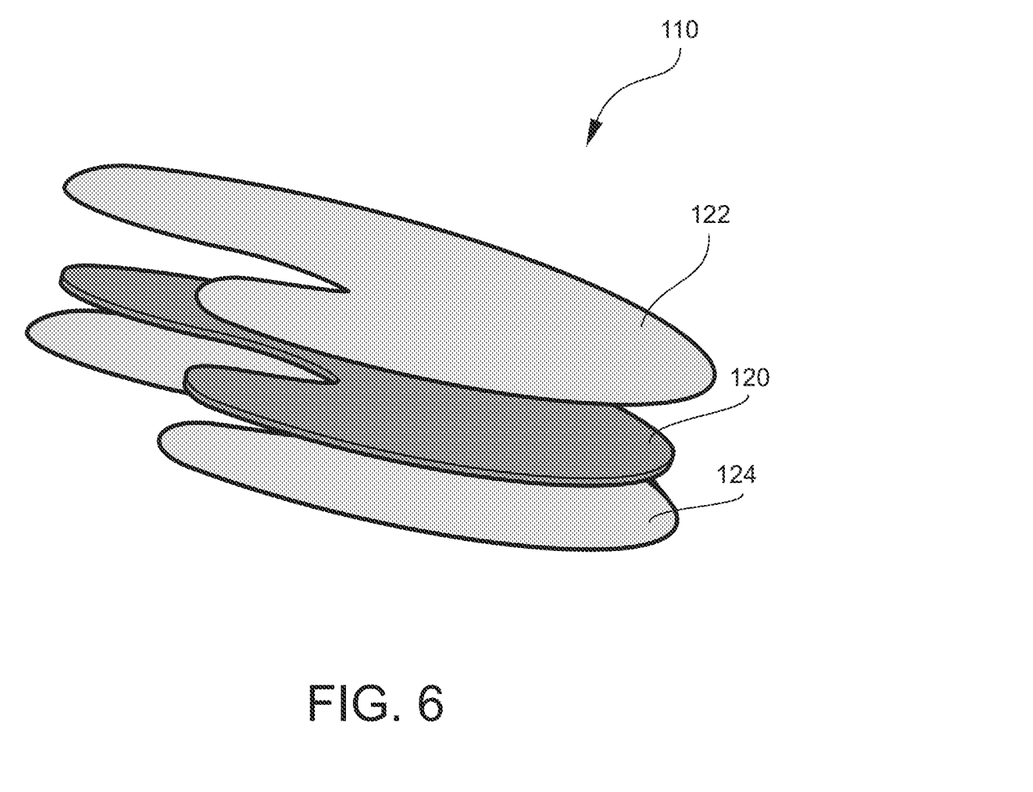
FIG. 6 is an exploded view of an alternative embodiment of the present invention.

In another alternative embodiment of the present invention and as illustrated in FIGS. 4-6, the sleep device 110 contains a top portion, a bottom portion, a first side, and a second side. The first side is generally convexly shaped, and the second side includes the two knobs 114, 116 and the cavity 118. The uppermost portion 128 of the first side, is generally the area where a person's nose and check is located and the first side extends downwardly in both directions on either side of the uppermost portion 128. A portion of the first side extends towards a user's forehead and behind the forehead, and the other portion of the first side extends towards a user's jaw. The user's ear is received within the cavity 118 and the end of the knob 114 is positioned adjacent the top of the ear, and the knob 116 is positioned adjacent the ear lobe.

The preferred dimensions of the sleep device 110 are illustrated in FIG. 4. However, it should be noted other dimensions may be utilized. For example, the length of the sleep device may be between about 2 inches to about 10 inches (including all points in-between), preferably between about 4 inches to about 9 inches (including all points in-between), and more preferably about 8 inches. The distance between A-A, as illustrated in FIG. 4, may be between about 1 inch to about 6 inches (including all points in-between), preferably between about 2 inches to about 5 inches (including all points in-between), and more preferably about $3^{31}/_{32}$ inches. The distance between B-B is $2^{19}/_{32}$ inches. The distance between C-C may be between about 1 inch to about 5 inches (including all points in-between), preferably between about 1½ inches to about 4 inches (including all points in-between), and more preferably about $2^{13}/_{32}$ inches.

The sleep device 110 may be composed of a core 120, enclosed in a first layer of foam 122 and a second layer of foam 124. By way of example only, the core 120 may be semi-rigid and composed of HDPE and the first piece and second piece of padded foam 122, 124 are a foamed HDPE. However, any other suitable material that is semi-rigid may be utilized as the core 120. Additionally, any suitable material that is padded or foamed may be utilized as the exterior to provide a cushion for the user. In another alternative embodiment, the sleep device 110 just contains a core without any padding covering the core.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A sleep device for receiving the side of a user's head to prevent bedding from putting pressure on the soft tissue of the user's face comprising:
    a core, being sized to fit on a pillow, having a top portion, a bottom portion, a top edge, a bottom, a first edge, and a second edge, wherein the first edge is opposite the second edge, the first edge is convexly shaped and the second edge includes a first knob and a second knob, the first edge includes an uppermost portion for receiving the side of the user's head and the first edge extends downwardly in both directions; and a concentrically shaped cavity is positioned between the first knob and the second knob, the cavity having a width of 3 inches or less for receiving a user's ear to prevent excessive pressure on said ear;
    a first layer of high density foam engaged with the bottom portion of the core and a second layer of high density foam engaged with the top portion of the core, wherein the first layer of high density foam and the second layer of high density foam have substantially the same shape as the core; and the total thickness of the core, the first layer of high density foam and the second layer of high density foam have a combined thickness of 0.5 inches or less.

2. The sleep device according to claim 1, wherein the distance between the first edge and the second edge is between 2 inches to 5 inches.

3. The sleep device according to claim 1, wherein the first knob and the second knob have a length between 1.5 inches to 4 inches.

4. The sleep device according to claim 1, wherein the core is semi-rigid and composed of HDPE and the first layer of foam and the second layer of foam are composed of foamed HDPE.

5. The sleep device according to claim 1, wherein the length between the top edge and the bottom edge of the sleep device is between 8 inches to 10 inches.

6. The sleep device according to claim 1, wherein the length between the top edge and the bottom edge of the sleep device is between 4 inches to 9 inches.

* * * * *